United States Patent [19]
Kennedy

[11] Patent Number: 5,207,325
[45] Date of Patent: May 4, 1993

[54] INSTRUMENT STORAGE TRAY

[76] Inventor: Patricia B. Kennedy, Box 810 Emerson Dr., Charlottesville, Va. 22901

[21] Appl. No.: 879,091

[22] Filed: May 1, 1992

Related U.S. Application Data

[63] Continuation of Ser. No. 728,340, Jul. 11, 1991, abandoned.

[51] Int. Cl.⁵ ............................................. B65D 81/18
[52] U.S. Cl. ..................................... 206/370; 206/511; 206/564
[58] Field of Search ............... 206/557, 562, 564, 561, 206/511, 363, 370, 438, 509

[56] References Cited

U.S. PATENT DOCUMENTS

| | | | |
|---|---|---|---|
| 508,700 | 11/1893 | Gruebel | 206/564 |
| 3,327,841 | 6/1967 | Schurman et al. | 206/564 X |
| 4,441,615 | 4/1984 | Goodrich | 206/511 |
| 4,458,815 | 7/1984 | Mollman et al. | 206/511 |
| 4,501,363 | 2/1985 | Isbey, Jr. | 206/564 X |
| 4,595,102 | 6/1986 | Cianci et al. | 206/370 X |
| 4,747,172 | 5/1988 | Hohol et al. | 206/557 X |
| 4,798,292 | 1/1989 | Hauze | 206/363 X |
| 5,011,718 | 4/1991 | Patterson | 206/363 X |
| 5,040,328 | 8/1991 | Coon | 206/557 X |

Primary Examiner—Jimmy G. Foster
Assistant Examiner—Jacob K. Ackun, Jr.
Attorney, Agent, or Firm—Seymour Levine

[57] ABSTRACT

An instrument storage tray is provided that is compartmentalized for the storage of instruments of various sizes and for the storage of instruments of given configurations. The tray has slots at the wall junctions and legs extending from the wall junctions configured for insertion of the legs of one tray in to the slots of another tray so that a plurality of trays may be transported at one time.

6 Claims, 1 Drawing Sheet

INSTRUMENT STORAGE TRAY

This is a continuation of co-pending application Ser. No. 07/728,340 filed on Jul. 11, 1991, abandoned.

BACKGROUND OF THE INVENTION

1. Field of the Invention

The invention relates to the field of surgical instrument holders, and more particularly to trays for providing an organized, efficient instrument arrangement.

2. Description of the Prior Art

Trays for holding surgical instruments are presently constructed of wire mesh to provide trays that are relatively light. In many instances instruments positioned in these trays are entangled in the wire mesh, rendering them difficult to extract. Some instruments, as for example knives, may slip through the wire mesh and may be damaged or may make contact with non-sterile objects rendering them unfit for use. Instruments protruding through the wire mesh may also inflict injury to the staff. Further, instruments placed in the trays are often of various sizes. Thus, smaller instruments may slide below larger ones, rendering them difficult to locate and subjecting them to damage from the weight of the larger and heavier instruments. Additionally, locating instruments of various sizes in these wire mesh trays is wasteful of space, since open areas are created in the trays due to the size variations.

SUMMARY OF THE INVENTION

In accordance with the principles of the present invention, a tray for holding surgical instruments is constructed of a high temperature resistant thermoplastic material and has an storage area between two pairs of parallel walls, each pair having a predetermined height above a base. The storage area is perforated to allow steam through the thermoplastic material and is defined by a length which is equal to the length of the one pair of parallel walls and a width which is equal to the length of the second pair of parallel walls. A shelf, having a height that is less than the height of the walls, is located within the storage area and extends the full distance between the first pair of parallel walls and from one wall of the second pair of parallel walls for a distance that is less than the length of the first pair of parallel walls. The distance between the end of the shelf and the second wall of the second pair of parallel walls has a depth which is appropriate for storing instruments that are generally larger than the instruments that would be stored on the shelf. A trough, located along one wall of the first pair of parallel walls has a width that is appreciably less than the storage area width and a length that is less than the length of the shelf, is provided for storing instruments, such as knives, that have long and narrow dimensions.

In a second embodiment of the invention, the shelf extends between the first pair of parallel without the trough and recessed slots are inserted in the shelf top which are shaped to accept instruments of a particular form. The area between shelf end and the second wall of the first pair of parallel walls accommodates instruments that are not configured for insertion in the slots on the shelf top.

In both embodiments legs are provided at the corners formed by the intersection of the two pairs of parallel walls. These corners and the legs are configured to allow tray stacking in a manner that eliminates contact of the stored instruments with the bottom of the tray above. This stacking, and handles formed in the second pair of parallel walls, facilitate the movement of a plurality of trays and provides instrument availability during an operation without interruption.

DESCRIPTION OF THE PREFERRED EMBODIMENTS

Figure 1:
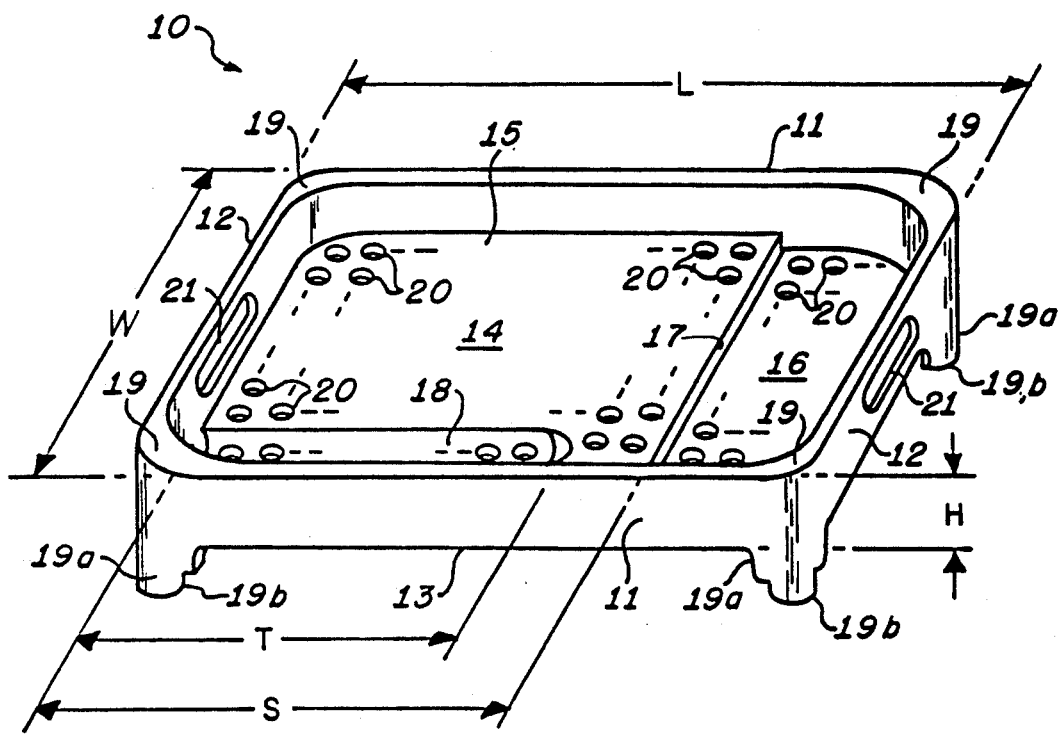
FIG. 1 is a pictorial representation of a first preferred embodiment of the invention.

Refer to FIG. 1, wherein an instrument storage tray 10 in accordance the invention is shown. This tray may be constructed of a high temperature resistant thermoplastic material, such as ULTIM manufactured by E. I. DuPont de Nemours & Co.,Inc. The tray may have a first pair of parallel walls 11 having a length L, which may be equal to twenty-three inches, and a second pair of parallel walls 12 generally perpendicular to the first pair of parallel walls and having a length W, which may be equal to eleven inches, enclose a base 13 to define a storage area 14. A shelf 15 within the storage area has a surface which may be one inch below the top of the walls 11 and 12 and one and one-quarter inches above the base 13. This shelf may extend from one wall of the second pair of parallel walls 12 for a distance S, which may be equal to nineteen inches. The surface of the shelf 15 is utilized for storing instruments of comparable size. Instruments having sizes greater than those stored on the shelf 15 may be placed in the recessed area 16 formed between the edge plate 17 of the shelf 14 and the second wall of the second pair of parallel walls 12. This recessed area has a depth, from the top of the shelf 15, which may be equal to one-half inch. A recessed trough 18 is provided for storing long narrow instruments, such as knives. This trough extends along one wall of the first pair of parallel walls 11 for a length T from one wall of the second pair of parallel walls 12, which may be ten inches, has a width, which may be one and one-half inches, and a depth from the top of the shelf 14, which may be one inch. Perforations 20, only a few of which are shown for clarity, extend from all surfaces through the bottom of the tray to permit sterilizing steam to contact all instrument surfaces.

Tray stacking slots 19, formed at the intersections of the walls 11 and 12, and legs 19a, extending from the walls at the intersections, are provided for tray stacking. The legs 19a may be configured with indents 19b to establish a space between the base of upper tray and the instruments in the lower tray. Alternatively, the walls 11 and 12 may be of a height that permits the base of the upper tray to sit on the walls of the lower tray without contacting the instruments in the lower tray, thus eliminating the need for the indents 19b.

Carrying slots 21 may be inserted in the second pair of parallel walls 12 to facilitate carrying of a tray or a stack of trays. These slots 21 may be three inches long and an inch high. Though slots in the walls 12 have been described, it should be recognized that indents of similar dimensions may be provided to facilitate carrying.

Figure 2:
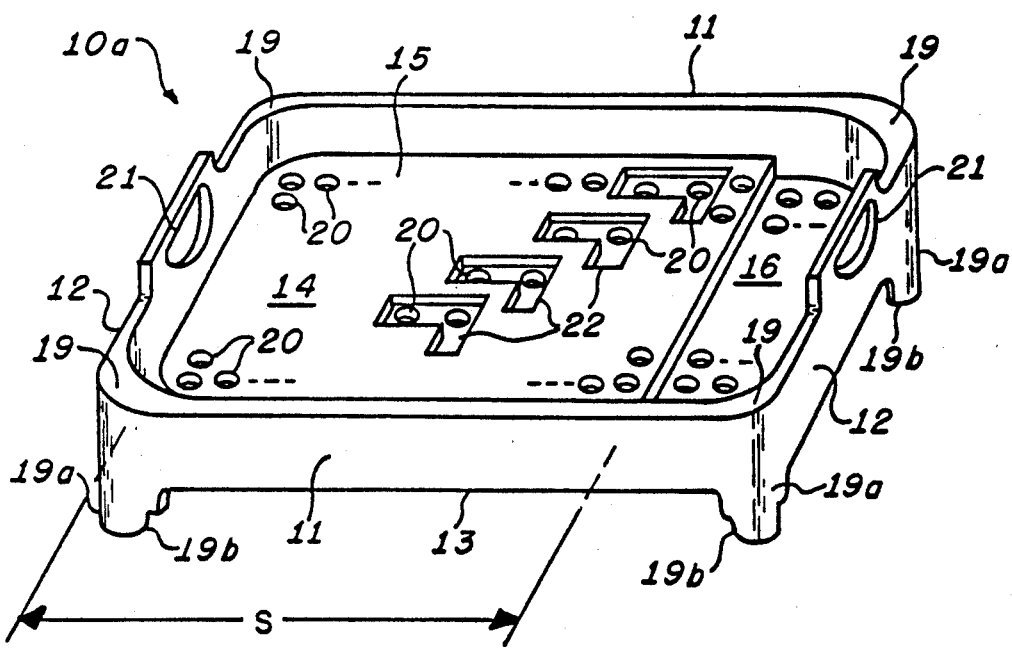
FIG. 2 is a pictorial representation of a second preferred embodiment of the invention.

Refer now to FIG. 2, wherein elements previously discussed bare the initially assigned reference numbers. In this second preferred embodiment 10A, which may also be constructed of the aforementioned ULTIM material, first 11 and second 12 pairs of parallel walls and a base 13 provide an instrument storage area 14. A shelf 15 may extend from the one wall of the second pair of parallel walls 12 for a distance S, which may be twenty-one inches, providing a recessed area having a length which may be two inches. As stated above, this recessed area provides storage space for instruments that are not conveniently accommodated on the shelf 15. Recessed slots 22 formed on the surface of the shelf 15 are configured to accept instruments having the same configuration. Thus each instrument has a place on the tray and missing instruments may be easily identified. Perforations 20, extending through the base, to permit sterilizing steam to contact all instrument surfaces, are provided from the bottom of each of the recessed slots 20 and from all surfaces of the tray.

Tray stacking slots 19, formed at the intersections of the walls 11 and 12, and legs 19a, extending from the walls at the intersections, are provided for tray stacking. The legs 19a may be configured with indents 19b to establish a space between the base of upper tray and the instruments in the lower tray. Alternatively, the walls 11 and 12 may be of a height that permits the base of the upper tray to sit on the walls of the lower tray without contacting the instruments in the lower tray, thus eliminating the need for the indents 19b.

Carrying slots 21 may be inserted in the second pair of parallel walls 12 to facilitate carrying of a tray or a stack of trays. These slots 21 may be three inches long and an inch high. Though slots in the walls 12 have been described, it should be recognized that indents of similar dimensions may be provided to facilitate carrying.

While the invention has been described in its preferred embodiments, it is to be understood that the words which have been used are words of description rather than of limitation and that changes within the purview of the appended claims may be made without departure from the true scope and spirit of the invention in its broader aspects.

I claim:

1. A tray for storing and sterilizing surgical instruments comprising:

first and second pairs of parallel walls each having a top and a bottom and a height H between said top and bottom, said first pair of parallel walls having a length L and said second pair of parallel walls extending between said first pair of parallel walls and having a width W therebetween, said first and second pairs of parallel walls establishing an instrument storage area;

an instrument storage shelf within said storage area having said width W, a length S extending from one wall of said second pair of parallel walls to an end plate extending down from said instrument storage shelf to a depth P, said length S being less than said length L, and positioned a distance h below aid top of said first and second paris of parallel walls said distance h being less than said height H;

a trough, having a base at a depth D below said instrument storage shelf, extending into said instrument storage self from one wall of said first pair of parallel walls to an edge at a width W from said one wall of said first pair of parallel walls, said width w being less than said width W, and extending from said one wall of said second pair of parallel walls to an end plate at a distance T, said distance T being less than said distance S;

a recessed instrument storage area extending between said first pair of parallel walls and from said end plate of said instrument storage shelf to a wall of said second pair of parallel walls other than said one wall of said second pair of parallel walls and having a base at said distance P below said instrument storage shelf; said depth D and said distance P being less than said height H;

said first and second pairs of parallel walls, said instrument storage shelf and end plate, said trough base, edge and end plate, and said recessed instrument storage area base constructed of a high temperature resistant thermoplastic material; and said instrument storage self, said base of said recessed instrument storage area, and said base of said trough having perforations for allowing steam to pass therethrough, such that instruments stored on said instrument storage shelf, in said recessed instrument storage area, and in said trough may be sterilized.

2. An instrument storage tray in accordance with claim 1 wherein each wall of said second pair of parallel walls has an indented area for gripping said tray.

3. An instrument storage tray in accordance with claim 1 wherein each wall of said second pair of parallel walls has a slot for carrying said tray.

4. An instrument storage tray in accordance with claim 1 further including means for stacking another instrument storage tray on said instrument storage tray and for stacking said instrument storage tray on a further instrument storage tray, said instrument storage tray, said another instrument storage tray, and said further instrument storage tray being similarly constructed.

5. An instrument storage tray in accordance with claim 4 wherein said stacking means comprises a slot formed at junctions of said first pair of parallel walls with said second pair of parallel walls and legs extending from said junctions, said slots and said legs constructed and arranged for stacking said another instrument storage tray on said instrument storage tray and for stacking said instrument storage tray on said further instrument storage tray, respectively.

6. An instrument storage tray in accordance with claim 1 wherein slots are formed in said instrument storage shelf that are configured to conform with that of instruments to be stored.

* * * * *